US012783783B2

(12) United States Patent
Misawa et al.

(10) Patent No.: US 12,783,783 B2
(45) Date of Patent: Nov. 3, 2026

(54) DOCUMENT PRESENTATION APPARATUS, DOCUMENT PRESENTATION METHOD, AND DOCUMENT PRESENTATION PROGRAM

(71) Applicant: FUJIFILM Corporation, Tokyo (JP)

(72) Inventors: Shotaro Misawa, Tokyo (JP); Taiki Furukawa, Nagoya (JP); Shintaro Oyama, Nagoya (JP); Nobuya Kitamura, Tokyo (JP); Hirokazu Yarimizu, Tokyo (JP); Kohei Onoda, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 230 days.

(21) Appl. No.: 18/749,507

(22) Filed: Jun. 20, 2024

(65) Prior Publication Data

US 2025/0021740 A1 Jan. 16, 2025

(30) Foreign Application Priority Data

Jul. 11, 2023 (JP) ................................. 2023-114076

(51) Int. Cl.
*G06F 3/048* (2013.01)
*G06F 40/103* (2020.01)
*G16H 15/00* (2018.01)

(52) U.S. Cl.
CPC ........... *G06F 40/103* (2020.01); *G16H 15/00* (2018.01)

(58) Field of Classification Search
None
See application file for complete search history.

(56) References Cited

U.S. PATENT DOCUMENTS 8,090,717 B1 * 1/2012 Bharat .................... G06F 16/93 707/731
2011/0295844 A1 * 12/2011 Sun ........................ G06Q 10/00 707/723
2018/0158005 A1 * 6/2018 Batrakov ......... G06Q 10/06311
2019/0197303 A1 6/2019 Kanada
2021/0133498 A1 * 5/2021 Zhang ..................... G06F 18/28
2024/0256582 A1 * 8/2024 Jain ..................... G06F 16/3329

FOREIGN PATENT DOCUMENTS

JP 2019115011 7/2019

* cited by examiner

*Primary Examiner* — Thanh T Vu
(74) *Attorney, Agent, or Firm* — JCIPRNET

(57) ABSTRACT

A document presentation apparatus acquires date information based on text information included in a document, extracts a plurality of the documents based on a set condition, and presents the document of which an evaluation value based on the date information acquired for each of the plurality of extracted documents is relatively high with priority over the document of which the evaluation value is relatively low.

18 Claims, 9 Drawing Sheets

DOCUMENT PRESENTATION APPARATUS, DOCUMENT PRESENTATION METHOD, AND DOCUMENT PRESENTATION PROGRAM

CROSS-REFERENCE TO RELATED APPLICATIONS

This application claims priority from Japanese Patent Application No. 2023-114076, filed on Jul. 11, 2023, the entire disclosure of which is incorporated herein by reference.

BACKGROUND

1. Technical Field

The present disclosure relates to a document presentation apparatus, a document presentation method, and a document presentation program.

2. Description of the Related Art

JP2019-115011A discloses a technology for extracting date information from a character string included in document image data and including the extracted date information in a file name of the document image data.

SUMMARY

Summary documents in which documents describing daily tasks are summarized for a certain period are created in various fields. For example, in the medical field, medical documents such as an electronic medical record and a radiology report are created daily, and a summary document in which medical practices for a predetermined period are summarized based on the created medical documents is created at a specific time such as a time of hospital discharge. However, causing a user such as a doctor to create the summary document by looking through all of the medical documents for the predetermined period burdens the user. Thus, in a case where an appropriate document can be presented from the created documents while the user creates the summary document, the burden of the user can be reduced, which is preferable.

The present disclosure has been conceived in view of the above circumstances, and an object of the present disclosure is to provide a document presentation apparatus, a document presentation method, and a document presentation program that can present an appropriate document while a user creates a summary document.

A document presentation apparatus of according to an aspect of the present disclosure is a document presentation apparatus comprising at least one processor, in which the processor is configured to acquire date information based on text information included in a document, extract a plurality of the documents based on a set condition, and present the document of which an evaluation value based on the date information acquired for each of the plurality of extracted documents is relatively high with priority over the document of which the evaluation value is relatively low.

In addition, a document presentation method according to another aspect of the present disclosure is a document presentation method comprising, via a processor included in a document presentation apparatus, acquiring date information based on text information included in a document, extracting a plurality of the documents based on a set condition, and presenting the document of which an evaluation value based on the date information acquired for each of the plurality of extracted documents is relatively high with priority over the document of which the evaluation value is relatively low.

In addition, a document presentation program according to still another aspect of the present disclosure is a document presentation program for causing a processor included in a document presentation apparatus to execute a process comprising acquiring date information based on text information included in a document, extracting a plurality of the documents based on a set condition, and presenting the document of which an evaluation value based on the date information acquired for each of the plurality of extracted documents is relatively high with priority over the document of which the evaluation value is relatively low.

According to the present disclosure, an appropriate document can be presented while a user creates a summary document.

DETAILED DESCRIPTION

Hereinafter, an embodiment of the disclosed technology will be described in detail with reference to the drawings.

Figure 1:
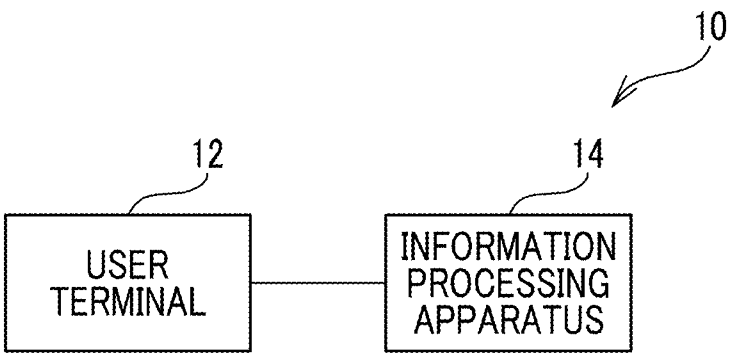
FIG. 1 is a block diagram illustrating an example of a configuration of an information processing system.

First, a configuration of an information processing system 10 according to the present embodiment will be described with reference to FIG. 1. As illustrated in FIG. 1, the information processing system 10 includes a user terminal 12 used by a user such as a doctor and an information processing apparatus 14. Examples of the user terminal 12 include a tablet computer and a personal computer. Examples of the information processing apparatus 14 include a server computer and a cloud server. The information processing apparatus 14 is an example of a document presentation apparatus according to the disclosed technology.

Each of the user terminal 12 and the information processing apparatus 14 is connected to a network and can transmit and receive data with each other.

Figure 2:
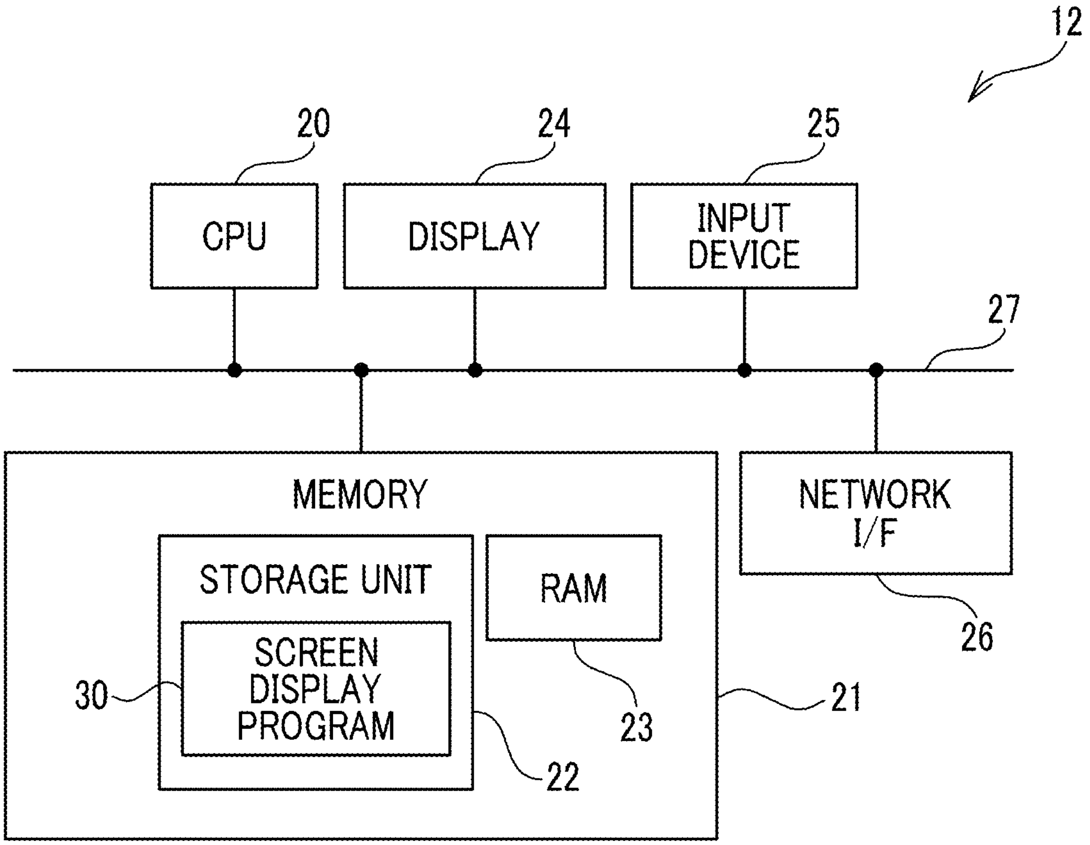
FIG. 2 is a block diagram illustrating an example of a hardware configuration of a user terminal.

Next, a hardware configuration of the user terminal 12 according to the present embodiment will be described with reference to FIG. 2. As illustrated in FIG. 2, the user terminal 12 includes a central processing unit (CPU) 20, a memory 21, a display 24, an input device 25, and a network interface (I/F) 26.

The CPU 20 implements various functions by executing a program stored in a storage unit 22, described later.

The memory 21 includes the storage unit 22 and a random access memory (RAM) 23. The RAM 23 is a memory for primary storage and is, for example, a RAM such as a static random access memory (SRAM) or a dynamic random access memory (DRAM).

The storage unit 22 is a non-volatile memory and is implemented by, for example, at least one of a hard disk drive (HDD), a solid state drive (SSD), or a flash memory. A screen display program 30 is stored in the storage unit 22 as a storage medium. The CPU 20 reads out the screen display program 30 from the storage unit 22, loads the screen display program 30 into the RAM 23, and executes the loaded screen display program 30.

The screen display program 30 is a program for displaying various screens on the display 24 based on data received from the information processing apparatus 14 through the network I/F 26. The screen display program 30 includes, for example, a web browser program.

The display 24 is a device that displays various screens and is, for example, a liquid crystal display or an electro luminescence (EL) display. The input device 25 is a device for a user to provide input and is, for example, at least any of a keyboard, a mouse, a microphone for audio input, a touchpad for proximity input including a contact, or a camera for gesture input. The network I/F 26 is an interface for connecting to a network. A bus 27 connects the CPU 20, the memory 21, the display 24, the input device 25, and the network I/F 26 to each other.

Figure 3:
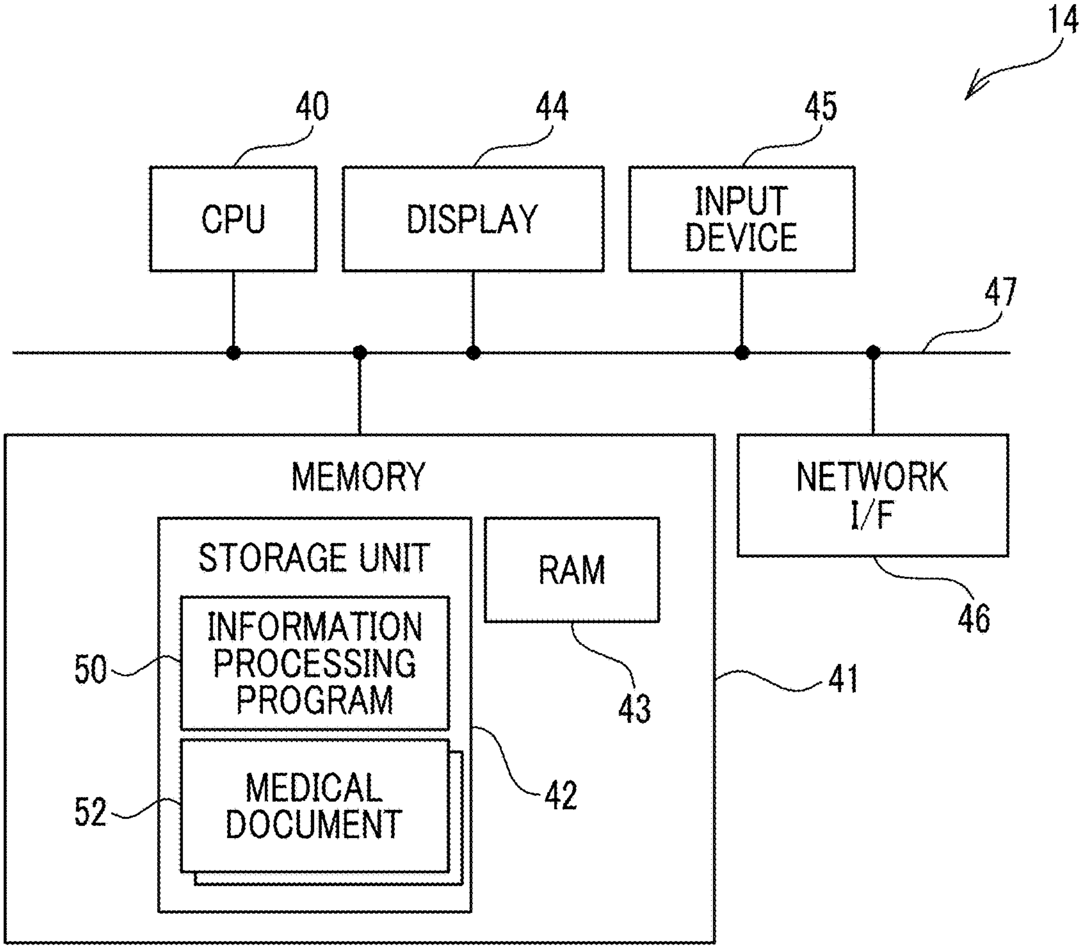
FIG. 3 is a block diagram illustrating an example of a hardware configuration of an information processing apparatus.

Next, a hardware configuration of the information processing apparatus 14 according to the present embodiment will be described with reference to FIG. 3. As illustrated in FIG. 3, the information processing apparatus 14 includes a CPU 40, a memory 41, a display 44, an input device 45, and a network I/F 46.

The CPU 40 implements various functions by executing a program stored in a storage unit 42, described later. The CPU 40 is an example of a processor according to the disclosed technology.

The memory 41 includes the storage unit 42 and a RAM 43. The RAM 43 is a memory for primary storage and is, for example, a RAM such as an SRAM or a DRAM.

The storage unit 42 is a non-volatile memory and is implemented by, for example, at least one of an HDD, an SDD, or a flash memory. An information processing program 50 is stored in the storage unit 42 as a storage medium. The CPU 40 reads out the information processing program 50 from the storage unit 42, loads the information processing program 50 into the RAM 43, and executes the loaded information processing program 50.

In addition, a plurality of medical documents 52 created by the user are stored in the storage unit 42. The medical document 52 is an example of a document according to the disclosed technology. The plurality of medical documents 52 are used for creating a summary document. In the present embodiment, a case where the user creates the summary document called a hospital discharge summary while viewing the plurality of medical documents 52 will be illustratively described. Examples of the medical document 52 include an electronic medical record. The medical document 52 is created for each patient, and identification information such as a patient ID of the patient is attached to the medical document 52 as attribute information. Accordingly, which patient is related can be identified. Which patient is related may also be identifiable by inputting the patient ID in a specific input field in the document or storing the medical document 52 in a folder for each patient. Similarly, a creation date of the medical document 52 can also be identified. The medical document 52 is not limited to the electronic medical record and may be a radiology report, a medical fee invoice called a receipt, or the like. In addition, the document used for creating the summary document is not limited to the medical document and may be, for example, a document such as a research diary. In this case, the user creates a research report by summarizing a plurality of research diaries created daily. In addition, for example, the document used for creating the summary document may be a daily report, and the summary document may be a weekly report, a monthly report, or the like in which the daily report is summarized. In addition, while a case where the medical document 52 is stored in the storage unit 42 of the information processing apparatus 14 has been illustratively described in the present embodiment, the disclosed technology is not limited to this aspect. For example, the medical document 52 may be stored in a separate data storage server and be acquired through a network.

The display 44 is a device that displays various screens and is, for example, a liquid crystal display or an EL display. The input device 45 is a device for the user to provide input and is, for example, at least any of a keyboard, a mouse, a microphone for audio input, a touchpad for proximity input including a contact, or a camera for gesture input. The network I/F 46 is an interface for connecting to a network. A bus 47 connects the CPU 40, the memory 41, the display 44, the input device 45, and the network I/F 46 to each other.

The user such as a doctor creates the medical document 52 such as the electronic medical record daily with respect to a hospitalized patient and creates a new document called the hospital discharge summary at the specific time such as the time of hospital discharge by summarizing the plurality of medical documents 52 created during a hospitalization period.

Figure 4:
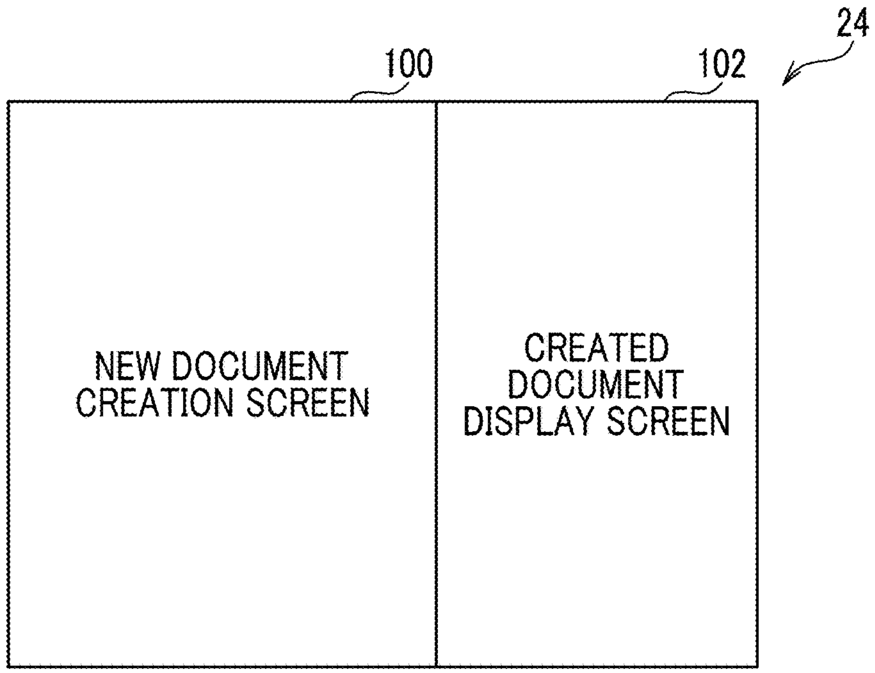
FIG. 4 is a diagram illustrating an example of a display screen.

As illustrated in FIG. 4, the information processing system 10 according to the present embodiment displays a new document creation screen 100 for creating the new document and a created document display screen 102 for displaying the medical document 52 as an example of a created document to be used for creating the new document, on the display 24 of the user terminal 12.

In a case where the user creates the medical document 52 in which medical practices related to a plurality of dates are summarized, it is considered to describe the medical practices and date information on which the medical practices are performed so that a time series of each medical practice can be perceived. Therefore, the information processing system 10 according to the present embodiment selects the medical document 52 to be presented to the user from the plurality of medical documents 52 based on the date information included in the medical document 52. Accordingly, the user can create the summary document, which is the new document, with reference to the medical document 52 which is considered to summarize a plurality of medical practices.

Figure 5:
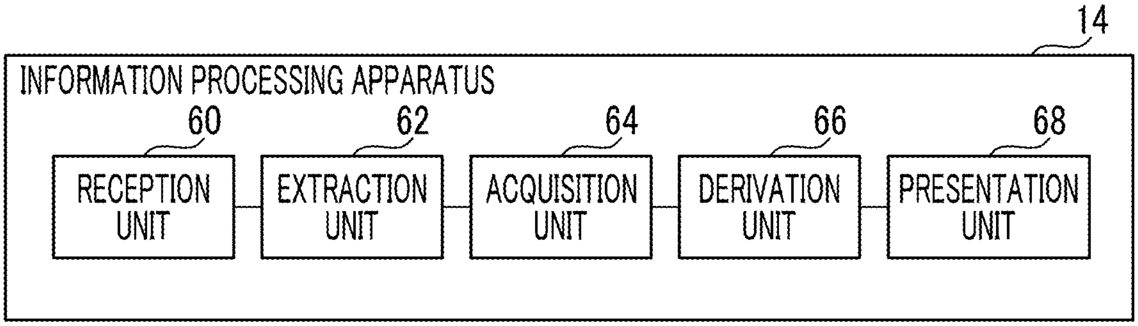
FIG. 5 is a block diagram illustrating an example of a functional configuration of the information processing apparatus.

Next, a functional configuration of the information processing apparatus 14 will be described with reference to FIG. 5. As illustrated in FIG. 5, the information processing apparatus 14 includes a reception unit 60, an extraction unit 62, an acquisition unit 64, a derivation unit 66, and a presentation unit 68. The CPU 40 functions as the reception unit 60, the extraction unit 62, the acquisition unit 64, the derivation unit 66, and the presentation unit 68 by executing the information processing program 50.

The reception unit 60 receives identification information of a patient (hereinafter, referred to as a "target patient") as a target for creating the new document and a period (hereinafter, referred to as a "creation target period") as a target for creating the new document. Examples of the creation target period include a hospitalization period in which the patient is hospitalized once. For example, the identification information of the target patient and the creation target period are input into the user terminal 12 by the user and are transmitted to the information processing apparatus 14 from the user terminal 12. Target periods may be stored in association with the identification information of the patients, and the target period corresponding to the patient may be derived in accordance with the input of the identification information of the patient provided by the user.

The extraction unit 62 extracts the plurality of medical documents 52 based on a set condition. In the present embodiment, an example in which a condition that the medical document 52 is created in the creation target period for the target patient received by the reception unit 60 is applied as the set condition will be described. That is, the extraction unit 62 extracts the plurality of medical documents 52 created for the target patient in the creation target period from the storage unit 42 using the identification information of the target patient and the creation target period received by the reception unit 60.

The acquisition unit 64 acquires the date information for each of the plurality of medical documents 52 extracted by the extraction unit 62 based on text information included in the medical document 52. For example, the acquisition unit 64 acquires the date information by extracting a character string indicating a date from the text information included in the medical document 52. In this case, the acquisition unit 64 may acquire the date information from the text information based on a rule such as a regular expression. In addition, in this case, the acquisition unit 64 may acquire the date information by inputting the text information included in the medical document 52 into a trained model that is a trained model obtained by machine learning and that takes input of the text information and outputs the date information included in the input text information.

Figure 6:
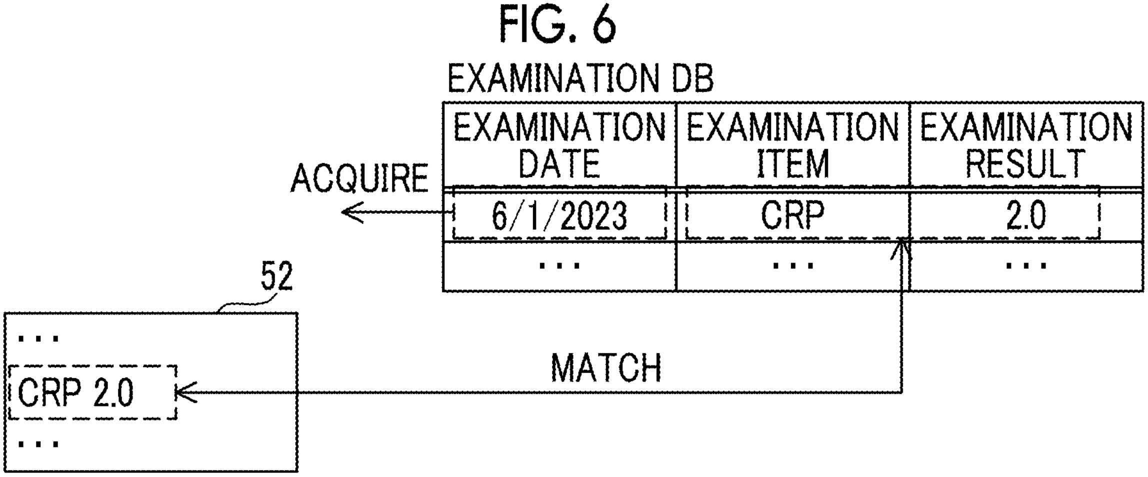
FIG. 6 is a diagram for describing an example of processing of acquiring date information.

The acquisition unit 64 may acquire the date information based on a medical practice or an examination result included in the text information and on data in which the medical practice or the examination result is associated with an execution date of the medical practice or the examination. Here, the execution date of the medical practice or the examination means a date registered as data. In addition, the medical practice means treatment such as surgery, administration, and the like. Specifically, for example, as illustrated in FIG. 6, the acquisition unit 64 may refer to a database in which an examination item, the examination result, and the execution date of the examination related to the target patient are associated with each other and acquire the execution date of the examination matching a combination of the examination item and the examination result included in the text information as the date information.

In addition, the date information may be information indicating a relative date based on a specific time, such as "○ days ago", "after ○ days of hospitalization", and "immediately after hospitalization".

The derivation unit 66 derives an evaluation value for each of the plurality of medical documents 52 extracted by the extraction unit 62 based on the date information acquired by the acquisition unit 64. In the present embodiment, the derivation unit 66 derives the evaluation value by counting the date information for each of the plurality of medical documents 52. That is, the evaluation value of the medical document 52 according to the present embodiment is the number of pieces of the date information acquired based on the text information of the medical document 52 and is a value indicating higher evaluation as the number of pieces of the date information is increased.

The derivation unit 66 may assign a weight to specific date information in deriving the evaluation value. In this case, in deriving the evaluation value, the derivation unit 66 may derive a degree of importance of the date information acquired for each of the plurality of medical documents 52 and assign the weight to the date information of which the degree of importance is greater than or equal to a threshold value. Specifically, the derivation unit 66 derives a default value of the degree of importance of the date information as "low" and derives the degree of importance of the date information corresponding to the execution date of at least one of the medical practice or the examination as "high". In this case, in deriving the evaluation value, the derivation unit 66 may set the evaluation value to a value indicating high evaluation by counting 1.5 for the date information of which the degree of importance is "high". In addition, the derivation unit 66 may refer to the medical fee invoice called the receipt and increase the degree of importance of the date information as added points on the date are increased.

In addition, the evaluation value of the medical document 52 may be a value indicating higher evaluation as a length of a period indicated by the date information is increased. Specifically, the evaluation value of the medical document 52 may be the number of days from the oldest date information to the newest date information acquired from the text information included in the medical document 52. In this case, for example, in a case where the date information acquired from the text information included in the medical document 52 is "4/1", "4/3", and "4/8", the evaluation value of the medical document 52 is "8" indicating the number of days from "4/1" to "4/8".

In addition, the evaluation value of the medical document 52 may be a total value of periods indicated by each date information acquired from the text information included in the medical document 52. In this case, for example, in a case where the date information acquired from the text information included in the medical document 52 is "4/1", "4/3", and "4/8", the evaluation value of the medical document 52 is "3" which is the total value of the periods indicated by each date information.

In addition, the derivation unit 66 may derive the evaluation value using only the date information indicating a date on or before the creation date of the medical document 52 among pieces of the date information acquired by the acquisition unit 64. Specifically, for example, in a case where the creation date of the medical document 52 is "4/1" and a text "scheduled to be discharged from hospital on 4/7" is included in the text information of the medical document 52, the derivation unit 66 may exclude and not use "4/7" which is a date after "4/1" in deriving the evaluation value.

The presentation unit 68 presents the medical document 52 of which the evaluation value derived by the derivation unit 66 is relatively high with priority over the medical document 52 of which the evaluation value is relatively low, for each of the plurality of medical documents 52 extracted by the extraction unit 62. In the present embodiment, the presentation unit 68 presents the medical document 52 to the user by outputting the medical document 52 to the user terminal 12 through the network I/F 46. At this point, the presentation unit 68 may output the creation date and the evaluation value of the medical document 52 by adding the creation date and the evaluation value to the medical document 52.

Specifically, the presentation unit 68 presents only the medical document 52 of which the evaluation value derived by the derivation unit 66 is greater than or equal to a threshold value among the plurality of medical documents 52 extracted by the extraction unit 62. Accordingly, the presentation unit 68 presents the medical document 52 of which the evaluation value is greater than or equal to the threshold value with priority over the medical document 52 of which the evaluation value is less than the threshold value.

Figure 7:
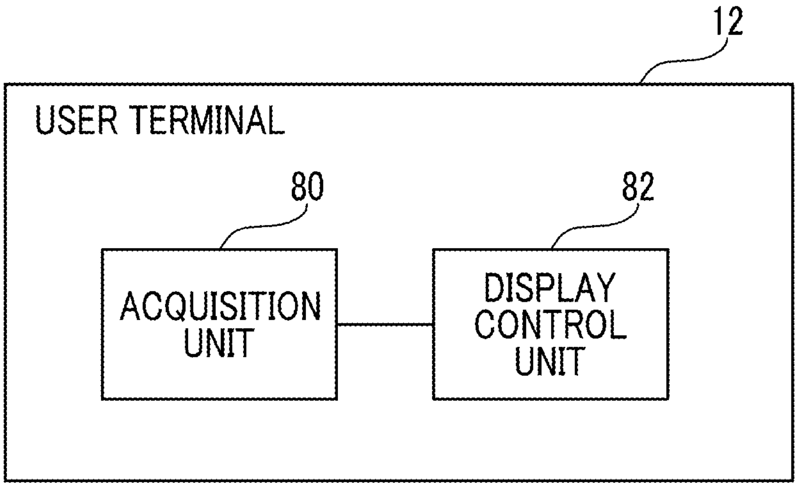
FIG. 7 is a block diagram illustrating an example of a functional configuration of the user terminal.

Next, a functional configuration of the user terminal 12 will be described with reference to FIG. 7. As illustrated in FIG. 7, the user terminal 12 includes an acquisition unit 80 and a display control unit 82. The CPU 20 functions as the acquisition unit 80 and the display control unit 82 by executing the screen display program 30.

The acquisition unit 80 acquires one or more medical documents 52 transmitted from the information processing apparatus 14 through the network I/F 26.

The display control unit 82, as described above, displays the new document creation screen 100 for creating the new document and the created document display screen 102 for displaying the medical document 52 to be used for creating the new document on the display 24 (refer to FIG. 4).

Figure 8:
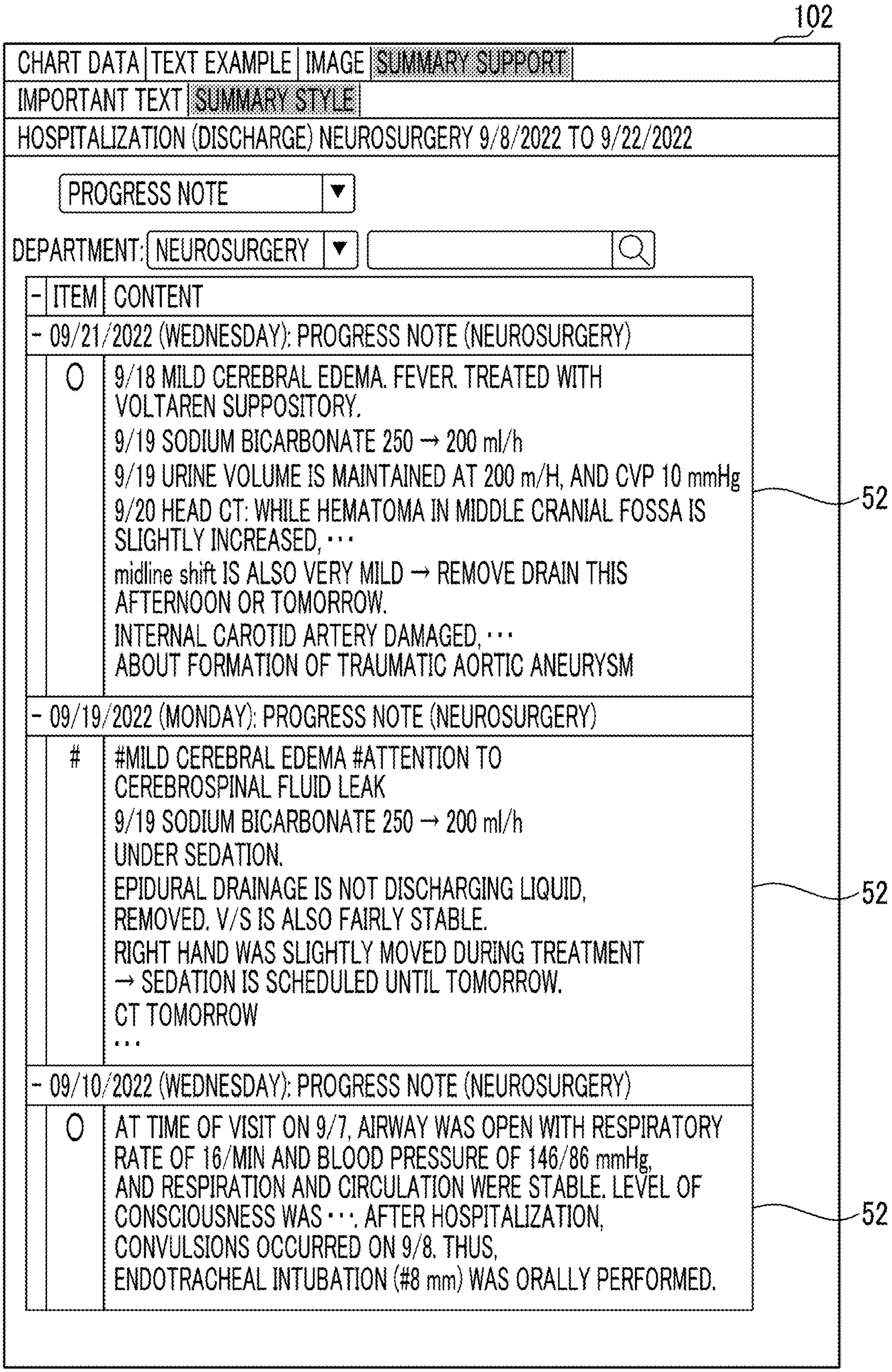
FIG. 8 is a diagram illustrating an example of a created document display screen.

As illustrated in FIG. 8, the display control unit 82 displays the medical document 52 acquired by the acquisition unit 80 on the created document display screen 102 in accordance with a predetermined display order. FIG. 8 illustrates an example in which the evaluation values of three medical documents 52 among the medical documents 52 created from "2022 Sep. 8" to "2022 Sep. 22" are greater than or equal to the threshold value and the three medical documents 52 are displayed in an order of the newest creation date. The display order of the medical documents 52 may be, for example, the order of the newest creation date, an order of the oldest creation date, or an order of the highest evaluation value. The display order in this case means an order of display positions.

In addition, in the example in FIG. 8, the plurality of medical documents 52 are displayed in a table form. One row of the table corresponds to one medical document 52, and a content column indicates content of the medical document 52. In addition, in the example in FIG. 8, an item column indicates a category of the medical document 52. Examples of the category include "Subject (subject information)", "Object (object information)", "Assessment (evaluation)", and "Plan (schedule)". In the example in FIG. 8, the item column describes an initial of a word indicating a corresponding category. In addition, the item column also describes "#" corresponding to a problem list. Here, a problem includes at least any of a medical abnormal event (illness) recognized in the patient by the doctor, a disease, a simple opinion, a past medical history, a social event, or the like.

The display control unit 82 may display the medical document 52 in an order of the highest evaluation indicated by the evaluation value on the created document display screen 102. In addition, the display control unit 82 may display the medical document 52 together with the evaluation value on the created document display screen 102. In addition, the display control unit 82 may display the medical document 52 of which the evaluation value is relatively high in a highlighted manner with respect to the medical document 52 of which the evaluation value is relatively low. In this case, for example, in a case where the plurality of medical documents 52 are displayed in a list in a table form, the display control unit 82 may change a background color in only a row of the medical document 52 of which the evaluation value is greater than or equal to a certain value. In addition, the display control unit 82 may display the medical document 52 of which the evaluation value is relatively low in a non-highlighted manner with respect to the medical document 52 of which the evaluation value is relatively high. In this case, for example, in a case where the plurality of medical documents 52 are displayed in a list in a table form, the display control unit 82 may gray out only a row of the medical document 52 of which the evaluation value is less than the certain value.

Figure 9:
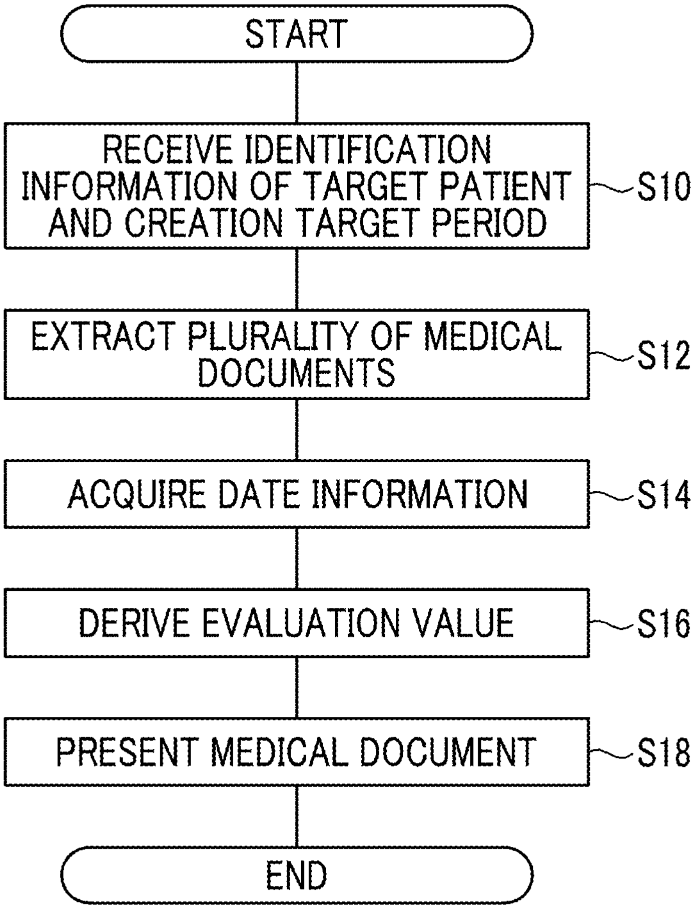
FIG. 9 is a flowchart illustrating an example of evaluation value derivation processing.

Next, an action of the information processing apparatus 14 will be described with reference to FIG. 9. Evaluation value derivation processing illustrated in FIG. 9 is executed by executing the information processing program 50 via the CPU 40. For example, the evaluation value derivation processing illustrated in FIG. 9 is executed in a case where an execution start instruction is input by the user.

In step S10 in FIG. 9, the reception unit 60 receives the identification information of the target patient and the creation target period. In step S12, the extraction unit 62 extracts the plurality of medical documents 52 created for the target patient in the creation target period from the storage unit 42 using the identification information of the target patient and the creation target period received in step S10. In step S14, the acquisition unit 64, as described above, acquires the date information based on the text information included in the medical document 52 for each of the plurality of medical documents 52 extracted in step S12.

In step S16, the derivation unit 66, as described above, derives the evaluation value based on the date information acquired in step S14 for each of the plurality of medical documents 52 extracted in step S12. In step S18, the presentation unit 68, as described above, presents the medical document 52 of which the evaluation value derived in step S16 is relatively high with priority over the medical document 52 of which the evaluation value is relatively low, for each of the plurality of medical documents 52 extracted in step S12. In a case where the processing in step S18 is finished, the evaluation value derivation processing is finished.

Figure 10:
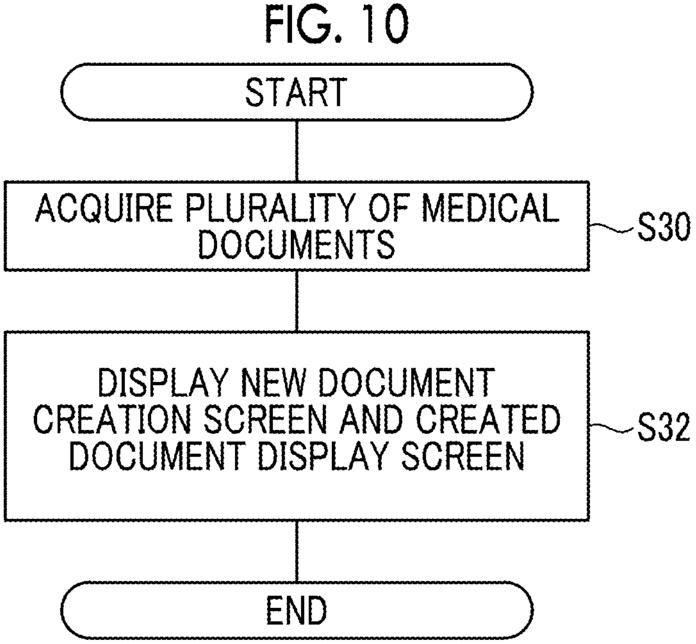
FIG. 10 is a flowchart illustrating an example of display control processing.

Next, an action of the user terminal 12 will be described with reference to FIG. 10. Display control processing illustrated in FIG. 10 is executed by executing the screen display program 30 via the CPU 20. For example, the display control processing illustrated in FIG. 10 is executed in a case where the user terminal 12 receives the medical document 52 transmitted from the information processing apparatus 14 through the processing in step S18.

In step S30 in FIG. 10, the acquisition unit 80 acquires one or more medical documents 52 transmitted from the information processing apparatus 14 through the network I/F 26. In step S32, the display control unit 82 displays the new document creation screen 100 for creating the new document and the created document display screen 102 for displaying the medical document 52 to be used for creating the new document on the display 24. At this point, the display control unit 82, as described above, displays the medical document 52 acquired in step S30 on the created document display screen 102 in the predetermined display order. In a case where the processing in step S32 is finished, the display control processing is finished.

As described above, according to the present embodiment, an appropriate document can be presented in a case where the user creates the summary document.

In the embodiment, the presentation unit 68 may present the medical document 52 of which the evaluation value is relatively high with priority over the medical document 52 of which the evaluation value is relatively low, by targeting the medical document 52 of which the evaluation value is greater than or equal to the certain value among the plurality of medical documents 52 extracted by the extraction unit 62.

In addition, in the embodiment, the presentation unit 68 is illustrated as displaying only the medical document 52 of which the evaluation value is greater than or equal to the threshold value, as an example of presenting the medical document 52 of which the evaluation value is relatively high with priority over the medical document 52 of which the evaluation value is relatively low. However, the disclosed technology is not limited to this aspect. The presentation unit 68 may present the medical document 52 in an order from the medical document 52 of which the evaluation value is relatively high. In this case, the display control unit 82 may display the medical document 52 acquired by the acquisition unit 80 in the order of the highest evaluation value on the created document display screen 102. The presentation unit 68 may output the medical document 52 and the evaluation value to the user terminal 12, and the display control unit 82 of the user terminal 12 may display the medical document 52 on the created document display screen 102 by arranging the medical document 52 in the order of the highest evaluation value. In addition, the display control unit 82 may display the medical document 52 on the created document display screen 102 by varying a display aspect in accordance with a magnitude of the evaluation value. Examples of a method of varying the display aspect in this case include a method of varying a background color or a method of varying a display color of a text. For example, the display control unit 82 may display the medical document 52 of which the evaluation value is relatively high in a highlighted manner with respect to the medical document 52 of which the evaluation value is relatively low. For example, in a case where the medical document 52 is displayed in a table form, the display control unit 82 may display a background color or a display color of a text of a cell indicating the medical document 52 of which the evaluation value is relatively high in a visually noticeable color with respect to the medical document 52 of which the evaluation value is relatively low, or may display a background color or a display color of a text of a cell indicating the medical document 52 of which the evaluation value is relatively low in a visually unnoticeable color with respect to the medical document 52 of which the evaluation value is relatively high.

Figure 11:
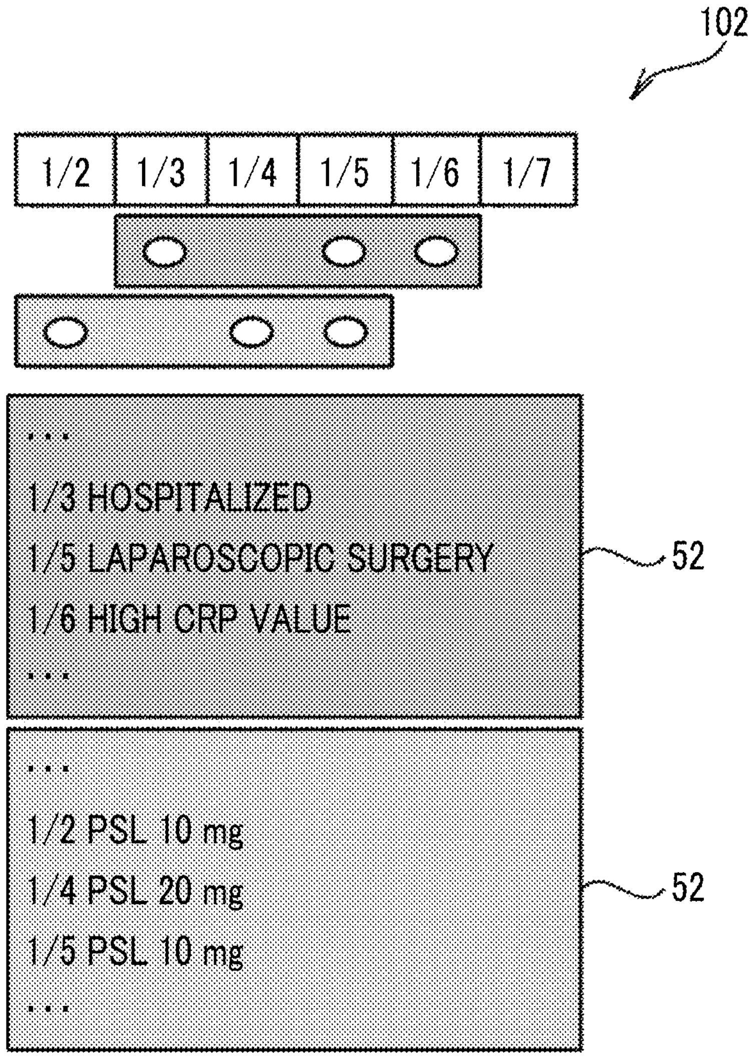
FIG. 11 is a diagram for describing an example of processing of presenting the date information.

In addition, in the embodiment, the presentation unit 68 may present the medical document 52 together with the date information acquired from the medical document 52. In this case, for example, as illustrated in FIG. 11, the display control unit 82 displays the medical document 52 together with the date information acquired from the medical document 52 on the created document display screen 102. In the example in FIG. 11, the date information included in the medical document 52 is set to be easily visible by displaying an ellipse below a date corresponding to the date information included in the medical document 52.

In addition, in the embodiment, the presentation unit 68 may present the medical document 52 together with the period indicated by the date information acquired from the medical document 52. In this case, for example, as illustrated in FIG. 11, the display control unit 82 displays the medical document 52 together with the period indicated by the date information acquired from the medical document 52 on the created document display screen 102. In the example in FIG. 11, the period indicated by the date information included in the medical document 52 is set to be easily visible using a solid gray rectangle corresponding to the period from the oldest date to the newest date in the date information included in the medical document 52. In addition, in this case, the display control unit 82 may set a correspondence relationship between the medical document 52 and the date information included in the medical document 52 to be easily perceived by setting a background color of the medical document 52 and a background color of the period indicated by the date information included in the medical document 52 to be the same color. In addition, for example, the display control unit 82 may initially display only the date information in an upper part in FIG. 11 and, in a case where the user selects one or more pieces of the date information, display the medical document 52 including the selected date information. In addition, for example, the display control unit 82 may initially display only the date information in the upper part in FIG. 11 and, in a case where the user selects two or more pieces of the date information in order, display the medical documents 52 including the selected date information in accordance with the order of selection. In addition, for example, the display control unit 82 may initially display only the medical document 52 in a lower part in FIG. 11 and, in a case where the user selects one or more medical documents 52, display the date information acquired from the selected medical document 52. In addition, for example, the display control unit 82 may initially display only the medical document 52 in the lower part in FIG. 11 and, in a case where the user selects two or more medical documents 52 in order, display the date information acquired from the selected medical documents 52 in accordance with the order of selection.

In addition, in the embodiment, the derivation unit 66 may derive a degree of similarity among the plurality of medical documents 52 extracted by the extraction unit 62. Examples of the degree of similarity among the medical documents 52 include an edit distance, a bilingual evaluation understudy (BLEU) score, a recall-oriented understudy for gisting evaluation (ROUGE) score, or a bidirectional encoder representations from transformers (BERT) score. In this case, the presentation unit 68 may present the medical document 52 of which the evaluation value is relatively high with priority over the medical document 52 of which the evaluation value is relatively low, for each of the plurality of medical documents 52 for which the degree of similarity derived by the derivation unit 66 is greater than or equal to a certain value.

Figure 12:
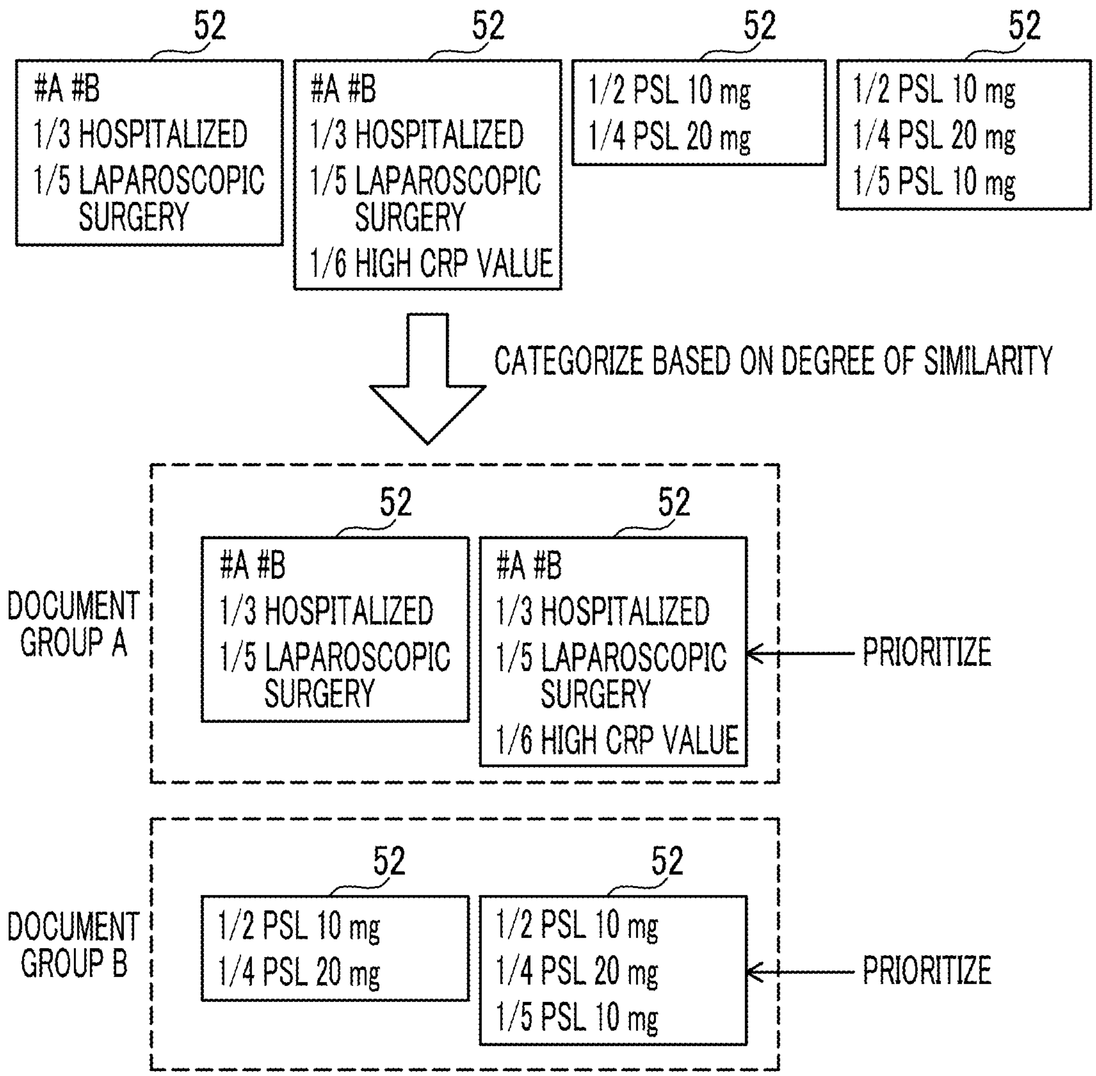
FIG. 12 is a diagram for describing an example of processing of presenting documents based on a degree of similarity between the documents.

In addition, as illustrated in FIG. 12, the presentation unit 68 may categorize the plurality of medical documents 52 extracted by the extraction unit 62 into a plurality of document groups based on the degree of similarity derived by the derivation unit 66. For example, the presentation unit

68 may categorize the plurality of medical documents 52 into the plurality of document groups such that the degree of similarity among the medical documents 52 is set to be greater than or equal to a certain value in each document group. In this case, the presentation unit 68, for each document group, may present the medical document 52 of which the evaluation value is relatively high with priority over the medical document 52 of which the evaluation value is relatively low, for each of the plurality of medical documents 52 belonging to the document group.

Figure 13:
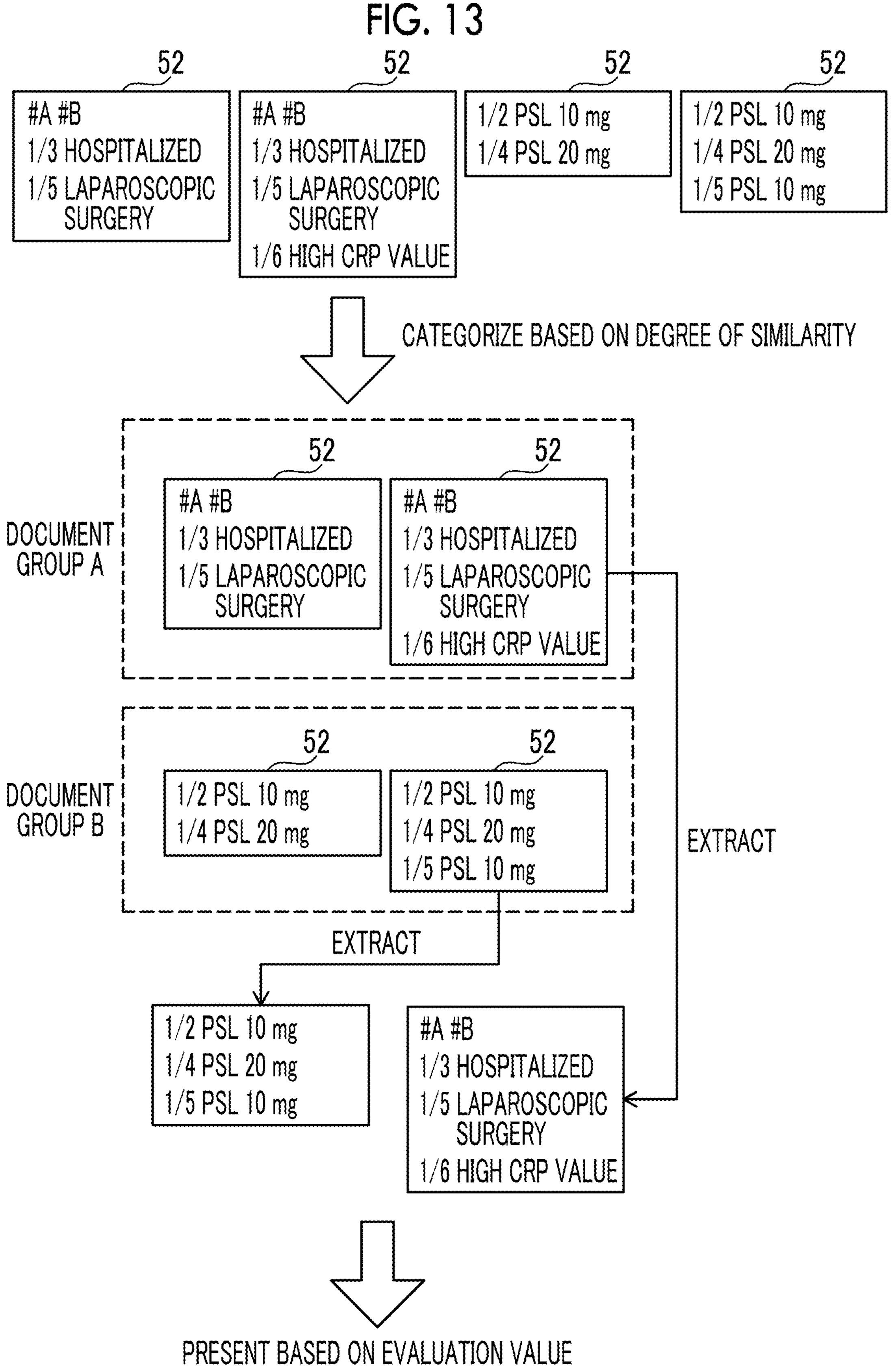
FIG. 13 is a diagram for describing an example of the processing of presenting the documents based on the degree of similarity between the documents.

In addition, as illustrated in FIG. 13, the presentation unit 68, for each document group, may extract the medical document 52 (hereinafter, referred to as a "highest document") of which the evaluation value is the highest from the plurality of medical documents 52 belonging to the document group. In this case, the presentation unit 68 may present the highest document of which the evaluation value is relatively high with priority over the highest document of which the evaluation value is relatively low, for each of a plurality of highest documents extracted for each document group.

The above degree of similarity among the medical documents 52 may be a degree of similarity of the entire text information included in the plurality of medical documents 52 extracted by the extraction unit 62. In addition, the degree of similarity among the medical documents 52 may be a degree of similarity of the date information acquired based on the text information included in the plurality of medical documents 52 extracted by the extraction unit 62. Furthermore, the degree of similarity among the medical documents 52 may be a combination of the degree of similarity of the entire text information and the degree of similarity of the date information.

In addition, in the embodiment, in a case where there are a plurality of combinations in which the date information acquired for each of the plurality of medical documents 52 covers the target period, the presentation unit 68 may set a combination of the medical documents 52 in which the number of medical documents 52 is relatively small as a presentation target. Examples of the target period in this case include the above creation target period. In addition, examples of the target period in this case include the period indicated by the date information of which the degree of importance is greater than or equal to the threshold value. In this case, the medical document 52 including the date information of which the degree of importance is greater than or equal to the threshold value is presented.

In addition, in the embodiment, in deriving the evaluation value, the derivation unit 66 may assign the weight to the date information in a case where there is a linefeed before the date information. In addition, the derivation unit 66 may derive a degree of change of a text described after each of a plurality of pieces of the date information included in the medical document 52 and, in a case where the degree of change is greater than or equal to a threshold value, may assign the weight to the date information used for deriving the degree of change. In addition, in a case where a specific keyword such as a current disease and past illness is included in the text described after the date information, the derivation unit 66 may assign the weight to the date information. In addition, the derivation unit 66 may set the evaluation value of the medical document 52 of which the creation date is relatively new to be a value indicating higher evaluation than the evaluation value of the medical document 52 of which the creation date is relatively old. In addition, the derivation unit 66 may assign the weight to the date information in accordance with the number of elapsed days from a reference date to the date information based on the reference date. The reference date may be at least any of, for example, a creation date of the new document or the creation date of the medical document 52 in which the date information is included. Specifically, in a case where the date information described in the medical document 52 created on "4/4" is "4/4", the date information indicates information about the creation date. Thus, it is highly likely that the medical document 52 is not a document that is summarized by including different dates. Meanwhile, in a case where the date information described in the medical document 52 created on "4/7" is "4/4", it is likely that the medical document 52 is a document in which information up to three days ago is summarized. Thus, the derivation unit 66 may set the evaluation value to a high value in accordance with the number of elapsed days from the creation date of the medical document 52 including the date information as a target for deriving the evaluation value.

Figure 14:
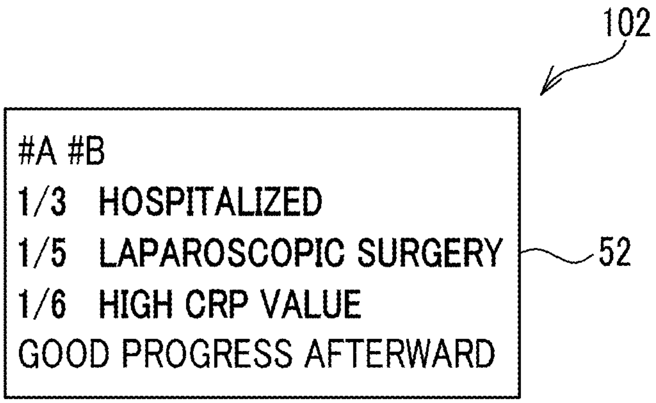
FIG. 14 is a diagram illustrating an example of the created document display screen.

In addition, in the embodiment, the presentation unit 68 may present the medical document 52 together with the date information used for deriving the evaluation value. In this case, for example, as illustrated in FIG. 14, the display control unit 82 may display the date information in an identifiable manner by displaying the date information used for deriving the evaluation value of the medical document 52 in a highlighted manner in displaying the medical document 52 on the created document display screen 102. Here, displaying in a highlighted manner is displaying in a noticeable manner and, for example, means displaying at least one of a text or a background of the text in a display color (for example, red) set as a noticeable color with respect to a display color (for example, black) as a reference. In the example in FIG. 14, a text with a bold font indicates a text displayed in a highlighted manner.

In addition, in the embodiment, at least a part of functional units comprised in the information processing apparatus 14 may be comprised in the user terminal 12, or at least a part of functional units comprised in the user terminal 12 may be comprised in the information processing apparatus 14. For example, the information processing apparatus 14 may generate the new document creation screen 100 and provide the new document creation screen 100 to the user terminal 12 in a streaming manner. In addition, each functional unit comprised in the user terminal 12 and in the information processing apparatus 14 may be comprised in one computer.

In addition, in the embodiment, for example, the following various processors can be used as a hardware structure of a processing unit that executes various types of processing, such as each functional unit of the user terminal 12 and each functional unit of the information processing apparatus 14. The various processors include, in addition to a CPU that is a general-purpose processor functioning as various processing units by executing software (program) as described above, a programmable logic device (PLD) such as a field programmable gate array (FPGA) that is a processor having a circuit configuration changeable after manufacture, a dedicated electric circuit such as an application specific integrated circuit (ASIC) that is a processor having a circuit configuration dedicatedly designed to execute specific processing, and the like.

One processing unit may be composed of one of the various processors or may be composed of a combination of two or more processors of the same type or different types (for example, a combination of a plurality of FPGAs or a combination of a CPU and an FPGA). In addition, a plurality of processing units may be composed of one processor.

As an example of the plurality of processing units composed of one processor, first, as represented by a computer such as a client and a server, a form of one processor that is composed of a combination of one or more CPUs and software and that functions as the plurality of processing units is possible. Second, as represented by a system on chip (SoC), a form of using a processor that implements functions of the entire system including the plurality of processing units in one integrated circuit (IC) chip is possible. Accordingly, various processing units are configured using one or more of the various processors as the hardware structure.

Furthermore, more specifically, an electric circuit (circuitry) in which circuit elements such as semiconductor elements are combined can be used as the hardware structure of the various processors.

In addition, while an aspect in which the screen display program 30 is stored (installed) in advance in the storage unit 22 has been described in each embodiment, the disclosed technology is not limited to this aspect. The screen display program 30 may be provided in a form of a recording on a recording medium such as a compact disc read only memory (CD-ROM), a digital versatile disc read only memory (DVD-ROM), and a universal serial bus (USB) memory. In addition, the screen display program 30 may be provided in a form of a download from an external apparatus through a network.

In addition, while an aspect in which the information processing program 50 is stored (installed) in advance in the storage unit 42 has been described in the embodiment, the disclosed technology is not limited to this aspect. The information processing program 50 may be provided in a form of a recording on a recording medium such as a CD-ROM, a DVD-ROM, and a USB memory. In addition, the information processing program 50 may be provided in a form of a download from an external apparatus through a network.

The following appendixes are further disclosed with respect to the above embodiment.

APPENDIX 1

A document presentation apparatus comprising at least one processor, in which the processor is configured to acquire date information based on text information included in a document, extract a plurality of the documents based on a set condition, and present the document of which an evaluation value based on the date information acquired for each of the plurality of extracted documents is relatively high with priority over the document of which the evaluation value is relatively low.

APPENDIX 2

The document presentation apparatus according to Appendix 1, in which the evaluation value is a value indicating higher evaluation as the number of pieces of the date information is increased.

APPENDIX 3

The document presentation apparatus according to Appendix 1, in which the evaluation value is a value indicating higher evaluation as a length of a period indicated by the date information is increased.

APPENDIX 4

The document presentation apparatus according to any one of Appendixes 1 to 3, in which the processor is configured to assign a weight to specific date information in deriving the evaluation value.

APPENDIX 5

The document presentation apparatus according to any one of Appendixes 1 to 4, in which the processor is configured to present the document of which the evaluation value is relatively high with priority over the document of which the evaluation value is relatively low, by targeting the document of which the evaluation value is greater than or equal to a certain value among the plurality of extracted documents.

APPENDIX 6

The document presentation apparatus according to any one of Appendixes 1 to 5, in which the processor is configured to derive the evaluation value using only date information indicating a date on or before a creation date of the document among pieces of the acquired date information.

APPENDIX 7

The document presentation apparatus according to any one of Appendixes 1 to 6, in which the processor is configured to acquire the date information based on a medical practice or an examination result included in the text information and on data in which the medical practice or the examination result is associated with an execution date of the medical practice or an examination.

APPENDIX 8

The document presentation apparatus according to any one of Appendixes 1 to 7, in which the processor is configured to derive a degree of similarity among the plurality of extracted documents, and present the document of which the evaluation value is relatively high with priority over the document of which the evaluation value is relatively low, for each of a plurality of the documents for which the degree of similarity is greater than or equal to a certain value.

APPENDIX 9

The document presentation apparatus according to any one of Appendixes 1 to 7, in which the processor is configured to derive a degree of similarity among the plurality of extracted documents, categorize the plurality of extracted documents into a plurality of document groups based on the derived degree of similarity, and present the document of which the evaluation value is relatively high with priority over the document of which the evaluation value is relatively low, for each of a plurality of the documents for each document group.

APPENDIX 10

The document presentation apparatus according to any one of Appendixes 1 to 7, in which the processor is configured to derive a degree of similarity among the plurality of extracted documents, categorize the plurality of extracted documents into a plurality of document groups based on the derived degree of similarity, extract a highest document of which the evaluation value is the highest for each document group, and present the highest document of which the evaluation value is relatively high with priority over the highest document of which the evaluation value is relatively low, for each of a plurality of the highest documents extracted for each document group.

APPENDIX 11

The document presentation apparatus according to any one of Appendixes 8 to 10, in which the degree of similarity is at least any of a degree of similarity of the text information included in each of the plurality of extracted documents or a degree of similarity of the date information acquired based on the text information included in each of the plurality of extracted documents.

APPENDIX 12

The document presentation apparatus according to any one of Appendixes 1 to 11, in which the processor is configured to present the document in an order from the document of which the evaluation value is relatively high.

APPENDIX 13

The document presentation apparatus according to any one of Appendixes 1 to 11, in which the processor is configured to present only the document of which the evaluation value is greater than or equal to a threshold value.

APPENDIX 14

The document presentation apparatus according to any one of Appendixes 1 to 13, in which the processor is configured to present the document together with the date information acquired from the document.

APPENDIX 15

The document presentation apparatus according to any one of Appendixes 1 to 13, in which the processor is configured to present the document together with a period indicated by the date information acquired from the document.

APPENDIX 16

The document presentation apparatus according to any one of Appendixes 1 to 15, in which the processor is configured to, in a case where there are a plurality of combinations in which the date information acquired for each of the plurality of documents covers a target period, set a combination of the documents in which the number of documents is relatively small as a presentation target.

APPENDIX 17

The document presentation apparatus according to Appendix 4, in which the processor is configured to derive a degree of importance of the date information acquired for each of the plurality of documents, and the specific date information is date information of which the degree of importance is greater than or equal to a threshold value.

APPENDIX 18

The document presentation apparatus according to Appendix 16, in which the processor is configured to derive a degree of importance of the date information acquired for each of the plurality of documents, and the target period is a period indicated by date information of which the degree of importance is greater than or equal to a threshold value.

APPENDIX 19

A document presentation method including, via a processor comprised in a document presentation apparatus, acquiring date information based on text information included in a document, extracting a plurality of the documents based on a set condition, and presenting the document of which an evaluation value based on the date information acquired for each of the plurality of extracted documents is relatively high with priority over the document of which the evaluation value is relatively low.

APPENDIX 20

A document presentation program for causing a processor comprised in a document presentation apparatus to execute a process including acquiring date information based on text information included in a document, extracting a plurality of the documents based on a set condition, and presenting the document of which an evaluation value based on the date information acquired for each of the plurality of extracted documents is relatively high with priority over the document of which the evaluation value is relatively low.

What is claimed is:

1. A document presentation apparatus comprising:

at least one processor, wherein the processor is configured to:

extract a plurality of documents based on a set condition;

acquire date information based on text information included in each of the plurality of extracted documents;

derive, for each of the plurality of extracted documents, an evaluation value using only the acquired date information determined based on the text information, wherein the acquired date information indicates a date on or before a creation date of each of the plurality of extracted documents among pieces of the acquired date information; and in response to determining that the evaluation value for each of the plurality of extracted documents is greater than or equal to a threshold value, filter and display only a document among the plurality of extracted documents corresponding to the evaluation value being greater than or equal to the threshold value on a screen.

2. The document presentation apparatus according to claim 1, wherein the evaluation value is a value indicating higher evaluation as a number of pieces of the date information is increased.

3. The document presentation apparatus according to claim 1, wherein the evaluation value is a value indicating higher evaluation as a length of a period indicated by the date information is increased.

4. The document presentation apparatus according to claim 1, wherein the processor is configured to assign a weight to specific date information in deriving the evaluation value.

5. The document presentation apparatus according to claim 4, wherein the processor is configured to derive a degree of importance of the date information acquired for each of the plurality of documents, and the specific date information is date information of which the degree of importance is greater than or equal to a threshold value.

6. The document presentation apparatus according to claim 1, wherein the processor is configured to present the document of which the evaluation value is relatively high with priority over the document of which the evaluation value is relatively low, by targeting the document of which the evaluation value is greater than or equal to a certain value among the plurality of extracted documents.

7. The document presentation apparatus according to claim 1, wherein the processor is configured to acquire the date information based on a medical practice or an examination result included in the text information and on data in which the medical practice or the examination result is associated with an execution date of the medical practice or an examination.

8. The document presentation apparatus according to claim 1, wherein the processor is configured to:

derive a degree of similarity among the plurality of extracted documents; and present the document of which the evaluation value is relatively high with priority over the document of which the evaluation value is relatively low, for each of a plurality of the documents for which the degree of similarity is greater than or equal to a certain value.

9. The document presentation apparatus according to claim 8, wherein the degree of similarity is at least any of a degree of similarity of the text information included in each of the plurality of extracted documents or a degree of similarity of the date information acquired based on the text information included in each of the plurality of extracted documents.

10. The document presentation apparatus according to claim 1, wherein the processor is configured to:

derive a degree of similarity among the plurality of extracted documents;

categorize the plurality of extracted documents into a plurality of document groups based on the derived degree of similarity; and present the document of which the evaluation value is relatively high with priority over the document of which the evaluation value is relatively low, for each of a plurality of the documents for each document group.

11. The document presentation apparatus according to claim 1, wherein the processor is configured to:

derive a degree of similarity among the plurality of extracted documents;

categorize the plurality of extracted documents into a plurality of document groups based on the derived degree of similarity;

extract a highest document of which the evaluation value is the highest for each document group; and present the highest document of which the evaluation value is relatively high with priority over the highest document of which the evaluation value is relatively low, for each of a plurality of the highest documents extracted for each document group.

12. The document presentation apparatus according to claim 1, wherein the processor is configured to present the plurality of extracted documents in an order of the highest evaluation value.

13. The document presentation apparatus according to claim 1, wherein the processor is configured to present the document together with the date information acquired from the document.

14. The document presentation apparatus according to claim 1, wherein the processor is configured to present the document together with a period indicated by the date information acquired from the document.

15. The document presentation apparatus according to claim 1, wherein the processor is configured to, in a case where there are a plurality of combinations in which the date information acquired for each of the plurality of documents covers a target period, set a combination of the documents in which the number of documents is relatively small as a presentation target.

16. The document presentation apparatus according to claim 15, wherein the processor is configured to derive a degree of importance of the date information acquired for each of the plurality of documents, and the target period is a period indicated by date information of which the degree of importance is greater than or equal to a threshold value.

17. A document presentation method comprising:

via a processor included in a document presentation apparatus, extracting a plurality of documents based on a set condition;

acquiring date information based on text information included in each of the plurality of extracted documents;

deriving, for each of the plurality of extracted documents, an evaluation value using only the acquired date information determined based on the text information, wherein the acquired date information indicates a date on or before a creation date of each of the plurality of extracted documents among pieces of the acquired date information; and in response to determining that the evaluation value for each of the plurality of extracted documents is greater than or equal to a threshold value, filtering and displaying only a document among the plurality of extracted documents corresponding to the evaluation value being greater than or equal to the threshold value on a screen.

18. A non-transitory computer-readable storage medium storing a document presentation program for causing a processor included in a document presentation apparatus to execute a process comprising:

extracting a plurality of documents based on a set condition;

acquiring date information based on text information included in each of the plurality of extracted documents;

deriving, for each of the plurality of extracted documents, an evaluation value using only the acquired date information determined based on the text information, wherein the acquired date information indicates a date on or before a creation date of each of the plurality of extracted documents among pieces of the acquired date information; and in response to determining that the evaluation value for each of the plurality of extracted documents is greater than or equal to a threshold value, filtering and displaying only a document among the plurality of extracted documents corresponding to the evaluation value being greater than or equal to the threshold value on a screen.

* * * * *